US010165971B2

(12) United States Patent
Omi (10) Patent No.: US 10,165,971 B2
(45) Date of Patent: Jan. 1, 2019

(54) DRIVER STATE DETERMINATION APPARATUS (71) Applicant: DENSO CORPORATION, Kariya, Aichi-pref. (JP)

(72) Inventor: Takuhiro Omi, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/506,064

(22) PCT Filed: Aug. 3, 2015

(86) PCT No.: PCT/JP2015/003904
§ 371 (c)(1),
(2) Date: Feb. 23, 2017

(87) PCT Pub. No.: WO2016/038784
PCT Pub. Date: Mar. 17, 2016

(65) Prior Publication Data
US 2018/0116579 A1    May 3, 2018

(30) Foreign Application Priority Data
Sep. 11, 2014    (JP) .................. 2014-184906

(51) Int. Cl.
*G08B 23/00*    (2006.01)
*A61B 5/18*    (2006.01)
*A61B 5/01*    (2006.01)
*A61B 5/08*    (2006.01)
*B60K 28/06*    (2006.01)
(Continued)

(52) U.S. Cl.
CPC .............. *A61B 5/18* (2013.01); *A61B 5/0075* (2013.01); *A61B 5/0077* (2013.01); *A61B 5/01* (2013.01); *A61B 5/015* (2013.01); *A61B 5/08* (2013.01); *A61B 5/0816* (2013.01); *A61B 5/6893* (2013.01); *A61B 5/7278* (2013.01); *A61B 5/7282* (2013.01); *B60K 28/06* (2013.01);
(Continued)

(58) Field of Classification Search
CPC ....... A61B 5/18; A61B 5/0075; A61B 5/0077; A61B 5/015; A61B 5/0816; A61B 5/6893
USPC ........................................ 340/575
See application file for complete search history.

(56) References Cited

U.S. PATENT DOCUMENTS 5,689,241 A * 11/1997 Clarke, Sr. ............... A61B 5/18
340/575
2005/0259849 A1    11/2005 Pavlidis
(Continued)

FOREIGN PATENT DOCUMENTS

JP    2003534864 A    11/2003
JP    2004334786 A    11/2004
(Continued)

Primary Examiner — John A Tweel, Jr.
(74) Attorney, Agent, or Firm — Harness, Dickey & Pierce, P.L.C.

(57) ABSTRACT

A driver state determination apparatus includes a far-infrared camera and a state determination section. The far-infrared camera takes facial images of a driver of a vehicle; the facial images are far-infrared images indicating a temperature distribution on a facial surface of the driver. The state determination section determines an abnormal state of the driver based on the far-infrared images sequentially taken by the far-infrared camera during a predetermined period.

14 Claims, 6 Drawing Sheets (51) Int. Cl.
*A61B 5/00* (2006.01)
*B60W 40/08* (2012.01)
*G06K 9/00* (2006.01)

(52) U.S. Cl.
CPC ......... *B60W 40/08* (2013.01); *G06K 9/00845* (2013.01); *B60K 28/066* (2013.01)

(56) References Cited

U.S. PATENT DOCUMENTS

| | | | |
|---|---|---|---|
| 2009/0268022 A1 | 10/2009 | Omi | |
| 2013/0010096 A1* | 1/2013 | S. .......................... | A61B 5/18 348/78 |

FOREIGN PATENT DOCUMENTS

| | | | |
|---|---|---|---|
| JP | 2007264785 A | 10/2007 | |
| JP | 2009183560 A | 8/2009 | |
| JP | 2009261516 A | 11/2009 | |
| JP | 2010194005 A | 9/2010 | |

* cited by examiner

IN STATES OF INHALING OR HOLDING BREATH

DRIVER STATE DETERMINATION APPARATUS

CROSS REFERENCE TO RELATED APPLICATIONS

This application is a U.S. National Phase Application under 35 U.S.C. 371 of International Application No. PCT/JP2015/003904 filed on Aug. 3, 2015 and published in Japanese as WO 2016/038784 A1 on Mar. 17, 2016. This application is based on and claims the benefit of priority from Japanese Patent Application No. 2014-184906 filed on Sep. 11, 2014. The entire disclosures of all of the above applications are incorporated herein by reference.

TECHNICAL FIELD

The present disclosure relates to a driver state determination apparatus that determines an abnormal state of a driver.

BACKGROUND ART

When a driver is in an abnormal state such as distractedness, doze, and seizure during driving a vehicle, the likelihood of causing an accident increases. Then, an apparatus that monitors a state of a driver has been proposed to prevent accidents.

A sleepiness detection apparatus in Patent Literature 1 detects facial parts such as eyes and a mouth from a facial image of a driver taken by a camera to detect sleepiness of the driver based on shapes of the facial parts. Monitoring of a state of a driver by measuring the pulse of the driver with a biosensor has been also proposed.

PRIOR ART LITERATURES

Patent Literature

Patent Literature 1: JP 2007-264785 A

SUMMARY OF INVENTION

When the shapes of driver's facial parts detected from a facial image are used, the accuracy in detection of the parts is reduced due to ambient light such as solar radiation and headlights of oncoming vehicles. This disadvantageously reduces the accuracy in determination of an abnormal state of the driver. When a biosensor is used, it is necessary to hold a driver. This is unsuitable for stable determination of the abnormal state of the driver. Further, biosensors using faint electrical signals are vehicle-noise sensitive.

It is an object of the present disclosure to provide a driver state determination apparatus that can determine an abnormal state of a driver accurately and stably.

According to an aspect of the present disclosure, a driver state determination apparatus is provided to include a far-infrared camera and a state determination section. The far-infrared camera takes facial images of a driver of a vehicle; the facial images are far-infrared images indicating a temperature distribution on a facial surface of the driver. The state determination section determines an abnormal state of the driver based on the far-infrared images sequentially taken by the far-infrared camera during a predetermined period.

The present aspect takes far-infrared images indicating a temperature distribution on the facial surface of a driver with a far-infrared camera. When the driver is in an abnormal state such as distractedness and sudden illness, breathing and blinking of the driver change to a different state from a normal state. When the breathing and blinking of the driver change from the normal state to a different state, a temperature distribution on the facial surface of the driver varies differently from in the normal state. Therefore, the abnormal state of the driver can be determined based on the temperature distribution indicated by the far-infrared images sequentially taken during a predetermined period. Far-infrared cameras are less susceptible to ambient light. Further, the far-infrared cameras, which are non-contact sensors, can stably take facial images of the driver. Therefore, the abnormal state of the driver can be determined from far-infrared images of the face of the driver accurately and stably.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

Hereafter, an embodiment that achieves a driver state determination apparatus is described in reference to the drawings.

Figure 1:
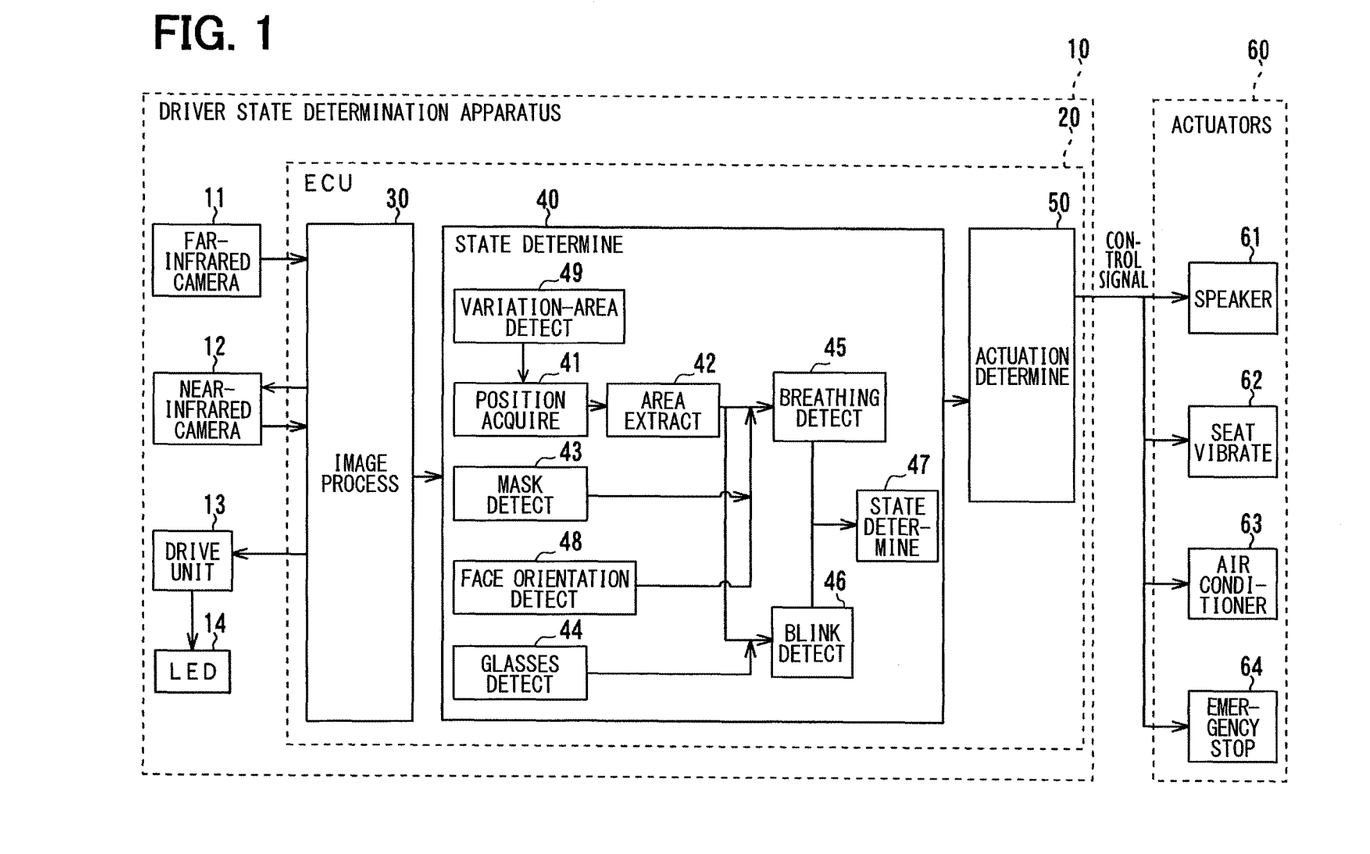
FIG. 1 illustrates a structure of a driver state determination apparatus of the present embodiment.
Figure 2:
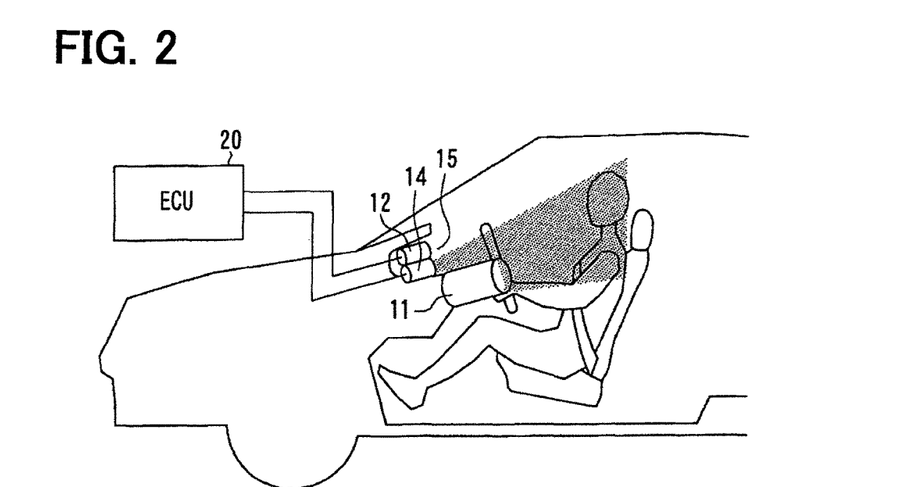
FIG. 2 illustrates mount positions of a near-infrared camera and a far-infrared camera.

First, a structure of a driver state determination apparatus 10 of the present embodiment is explained in reference to FIGS. 1 and 2. The driver state determination apparatus 10 includes an ECU 20, a far-infrared camera 11, and a near-infrared camera 12, and determines an abnormal state of a driver. In the present embodiment, the abnormal state of the driver signifies the state where the driver cannot perform appropriate recognitions, determinations, and manipulations required for driving. The state includes distractedness, doze, abnormal physical condition, and carelessness.

The far-infrared camera 11 is sensitive to a far-infrared area, and changes, into pixel values, an intensity of a far-infrared radiation emitted from a substance in an image taking area to generate a far-infrared image. Therefore, the far-infrared image indicates a temperature distribution of an imaged target, and temperature is higher as a pixel value is greater. The near-infrared camera 12 is sensitive to a near-infrared area, and takes an imaged target including an area illuminated by a projector 14 to generate a near-infrared image. The projector 14 is an illuminator that emits near-infrared light, and driven by a drive unit 13. The drive unit 13 is controlled by an image processing circuit 30 of the ECU 20 mentioned later. The projector 14 may use a light source having a filament in addition to an LED (light emitting diode). The LED is represented as an example herein.

The far-infrared camera 11 and near-infrared camera 12 take images of the area including the face area of the driver seated on the driver's seat from several to hundred times per a second. As in FIG. 2, the far-infrared camera 11 and near-infrared camera 12 are mounted near each other diagonally upward on a meter panel 15 to have elevation angles. The far-infrared camera 11 and near-infrared camera 12 are set to include the area containing the eyelids portion of the driver in the viewing angles. The near-infrared camera 12 has a wider field of view than the eyelids taken by the far-infrared camera 11. The eyelids portion is the area defined for each type of vehicle, and is the ellipse area where eye positions of various drivers having different physiques distribute at normal driving.

The far-infrared camera 11 and near-infrared camera 12 may be mounted not only on the meter panel 15 but also on the steering column. The far-infrared camera 11 and near-infrared camera 12 may be mounted to a position where the nasal cavity portions of the driver who is seated and faces forward can be taken.

The ECU 20 is also called a controller, and is a microcomputer including a CPU, ROM, RAM, and I/O as one example in the present embodiment. The CPU executes various programs in the ROM to realize multiple functions of the image processing circuit 30, a state determination circuit 40, and an actuation determination circuit 50. The ECU 20 can also achieve part or all of each of the multiple functions as a structure of hardware without depending on the programs.

The image processing circuit 30 sets the exposure timing and exposure time of the near-infrared camera 12 and the emission timing, emission time, and quantity of light of the projector 14 to transmit a control instruction to the near-infrared camera 12 and the drive unit 13 of the projector 14. The image processing circuit 30 acquires far-infrared images taken by the far-infrared camera 11 and near-infrared images taken by the near-infrared camera 12.

The state determination circuit 40 includes a position acquisition section 41, area extraction section 42, mask detection section 43, glasses detection section 44, breathing detection section 45 (also called a breathing state detection section), blink detection section 46 (also called a blink state detection section), state determination section 47, and face orientation detection section 48, and determines the abnormal state of the driver. Each section is mentioned later in detail. Each section is called a device.

When the state determination circuit 40 determines that the driver is abnormal, the actuation determination circuit 50 transmits a control signal to each apparatus 61 to 63 of an actuator group 60 to urge the driver to awaken and warn the driver. When the abnormal state continues, a control signal is transmitted to a vehicle emergency stop apparatus 64. In detail, the actuation determination circuit 50 transmits a control instruction to a speaker 61 to output an alarm and a warning message. The actuation determination circuit 50 transmits a control instruction to a seat vibration apparatus 62 installed to the driver's seat to vibrate the driver's seat. The actuation determination circuit 50 transmits a control instruction to an air conditioner 63 to blow cold wind to the driver. When the driver does not return from the abnormal state to normal state, the actuation determination circuit 50 transmits a control instruction to the vehicle emergency stop apparatus 64 to stop the vehicle emergently.

The actuation determination circuit 50 may drive two or more of the speaker 61, seat vibration apparatus 62, and air conditioner 63. The actuation determination circuit 50 may change or increase the apparatuses to be sequentially driven when the abnormal state continues. The apparatus that urges the driver to awaken may be other than the speaker 61, seat vibration apparatus 62, and air-conditioner 63. The actuator group 60 may only include at least one apparatus that urges the driver to awaken and the vehicle emergency stop apparatus 64.

Next, each section of the state determination circuit 40 is explained in reference to FIGS. 3 to 9. The position acquisition section 41 recognizes facial parts from near-infrared images, and acquires the positional informations on the recognized facial parts. The facial parts to be recognized include eyes, a nose, and a mouth. Specifically, the position acquisition section 41 processes a known technique such as template matching to recognize eyes, a nose, and a mouth from near-infrared images. The position acquisition section 41 acquires the positional informations on the recognized eyes, nose, and mouth, namely, coordinate informations on the images. The present specification uses "information" not only as uncountable noun but also as a countable noun. Information can also be equivalent to an information item.

Figure 3:
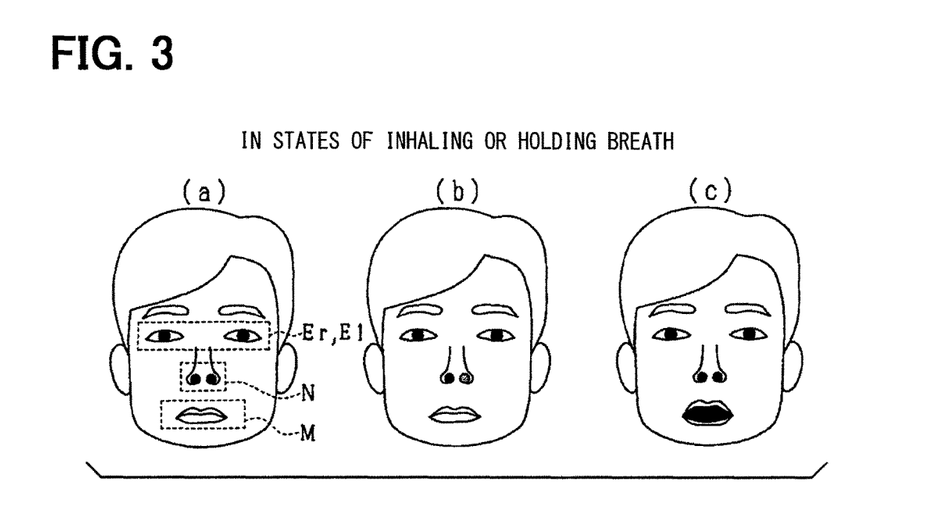
FIG. 3 is a schematic diagram indicating far-infrared images in states of inhaling or holding a breath.
Figure 4:
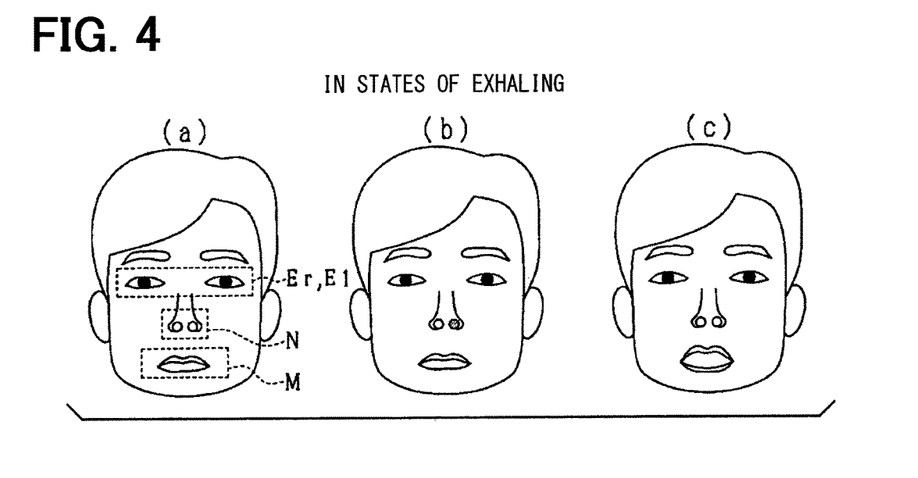
FIG. 4 is a schematic diagram indicating far-infrared images in exhalation states.
Figure 5:
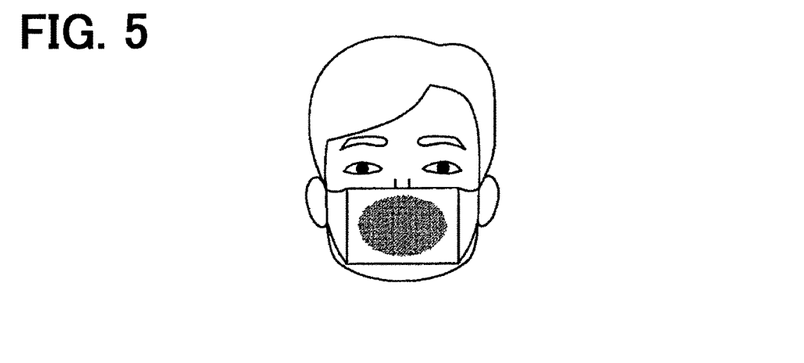
FIG. 5 is a schematic diagram indicating a far-infrared image in a state of wearing a mask.
Figure 6:
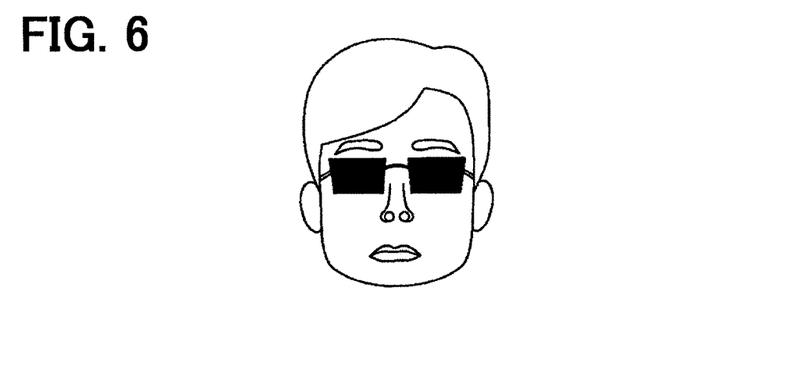
FIG. 6 is a schematic diagram indicating a far-infrared image in a state of wearing glasses.

As at (a) in FIG. 3 and at (a) in FIG. 4, the area extraction section 42 extracts eye areas Er, El, a nose area N, and a mouth area M from far-infrared images by using the positional informations acquired by the position acquisition section 41 and correspondences between coordinates of near-infrared images and coordinates of far-infrared images. The eye areas Er, El are illustrated integrally in the figures for convenience, but actually include two areas. The eye areas Er, El are search areas to search for eye portions including eyeballs. The nose area N is a search area to search for nasal cavity portions. The mouth area M is a search area to search for a mouth portion. The area extraction section 42 extracts areas centering the positional informations about the eyes, nose, and mouth as the eye areas Er, El, nose area N, and mouth area M, respectively. When the driver breathes through the nose, the nasal cavity portions are a breathing portion. When the driver breathes through the mouth, the mouth portion is a breathing portion.

Since far-infrared images have unclear edges of shapes unlike typical visible light images, it is difficult to recognize facial parts of a full face by using far-infrared images. Then, the area extraction section 42 extracts search areas by using the positional informations acquired from near-infrared images. The search areas are thus extracted to enable reduction in the load of searching far-infrared images for the eye portions, nasal cavity portions, and mouth portion and accurate detection of the eye portions, nasal cavity portions, and mouth portion.

The breathing detection section 45 detects a breathing state from the temperature variation informations on the nasal cavity portions or mouth portion. Relatively low temperature air flows into the nasal cavity portions or mouth portion by inhalation through the nose or mouth. Therefore, when the driver inhales from the nose or holds a breath, the nasal cavity portions of the far-infrared image have low brightness to appear dark as at (a) in FIG. 3. Since less air flows into the clogged nasal cavity portion of the driver, the clogged nasal cavity portion has higher brightness than the unclogged nasal cavity portion in the far-infrared image as at (b) in FIG. 3. When the driver inhales from the mouth or holds a breath, the mouth portion of the far-infrared image has low brightness to appear dark as at (c) in FIG. 3.

In contrast, relatively-high temperature air flows out of the nasal cavity portions or mouth portion by exhalation from the nose or mouth. Therefore, when the driver exhales from the nose, the nasal cavity portions of the far-infrared image increase in brightness to appear bright as at (a) in FIG. 4. When the nose of the driver is clogged, the brightness of the clogged nasal cavity portion becomes lower than that of the unclogged nasal cavity portion in the far-infrared image as at (b) in FIG. 4. When the driver exhales from the mouth or holds a breath, the mouth portion of the far-infrared image increases in brightness to appear bright as at (c) in FIG. 4.

Therefore, the temperature of the breathing portion in the far-infrared images taken during a predetermined period (for example, tens of seconds) varies with breathing. The breathing detection section 45 detects a breathing state such as a breathing cycle, breathing depth, and breath rate of the driver from the temperature variation information on the breathing portion, namely, the brightness variation information on the breathing portion in far-infrared images. The breathing cycle is an interval between peaks or between valleys in the brightness variation curve of the breathing portion as in FIG. 8. The breathing depth is a difference D between brightness of a peak and brightness of a valley in the brightness variation curve of the breathing portion as in FIG. 8.

When the mask detection section 43 detects a mask covering the nose and mouth of the driver, the breathing detection section 45 detects a breathing state from the temperature variation information on the mask by using the detected mask as the breathing portion.

The mask detection section 43 detects the mask from the far-infrared images taken during a predetermined period. It is difficult to detect a mask by extracting the mask, skin, and boundary from near-infrared images. In contrast, since the portion that covers the nose and mouth by the mask entirely varies in temperature with breathing in the far-infrared images as in FIG. 5, the mask is detectable from the far-infrared images during a predetermined period. When a larger area than the usual nose area N and mouth area M varies in temperature in the lower portion of the face, the mask detection section 43 detects the temperature variation area as the mask.

When the driver's face detected by the face orientation detection section 48 is oriented such that the nasal cavity portions are invisible by the far-infrared camera 11, the breathing detection section 45 stops detection of the breathing state. Since the nasal cavity portions are invisible when the face is tilted downward or upward greatly, the breathing detection section 45 stops detection of the breathing state. The face orientation detection section 48 detects an orientation of the face of the driver from the near-infrared images. In detail, the face orientation detection section 48 detects face orientations based on arrangement of the facial parts recognized in the near-infrared images.

The blink detection section 46 detects a blink state from the temperature variation informations on the eye portions. The surface temperature of an eyeball is lower than that of an eyelid. Therefore, when the driver opens the eyes, the eyeball portions of the far-infrared images decrease in brightness to appear dark. When the driver closes the eyes, the eyeball portions of the far-infrared images increase in brightness to appear bright.

Therefore, the eye areas Er, El in the far-infrared images taken during a predetermined period varies in temperature with blinking. The blink detection section 46 detects a blink state such as a blink cycle and eye closure duration of the driver from the temperature variation information on the eye areas Er, El, namely, the brightness variation informations on the eye areas Er, El in the far-infrared images. The blink cycle is an interval between peaks or between valleys on the brightness variation curve of the eye areas Er, El.

Figure 7:
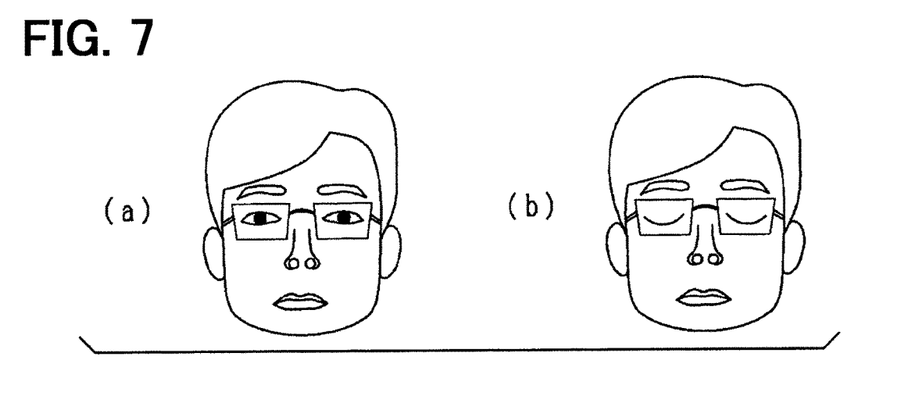
FIG. 7 is a schematic diagram indicating near-infrared images in a state of wearing glasses.

However, when the glasses detection section 44 detects the glasses of the driver, the blink detection section 46 detects an eye opening degree, which is an opening of the eyes of the driver, from the near-infrared images and detects a blink state from variation in the detected eye opening degree as at (a) and (b) in FIG. 7. In detail, the blink detection section 46 extracts the outlines of upper and lower eyelids from the near-infrared images, and detects an eye opening degree from an interval between the outlines of the extracted upper and lower eyelids and from the shapes of the outlines.

The glasses detection section 44 detects the glasses of the driver from the far-infrared images. The glasses portion always appears darker than the other face portions in the far-infrared images as in FIG. 6. Therefore, when a low-temperature portion is always present in the upper portion of the face in the far-infrared images, the glasses detection section 44 detects the low-temperature portion as the glasses.

The state determination section 47 determines the abnormal state of the driver based on the far-infrared images taken by the far-infrared camera 11 during a predetermined period. In detail, the state determination section 47 determines the abnormal state of the driver based on a breathing state and blink state of the driver.

Figure 8:
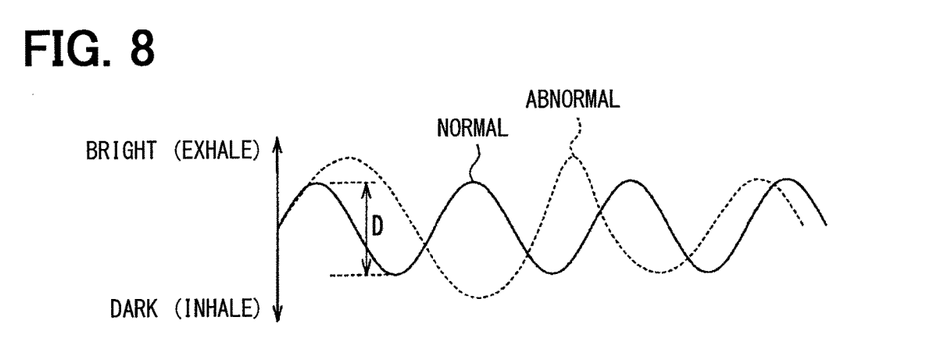
FIG. 8 illustrates breathing states in a normal state and an abnormal state.

As in FIG. 8, when the driver is normal, the breathing cycle and breathing depth indicate stable generally-constant values. When the driver is abnormal, the breathing cycle and depth change from the normal state to vary unstably. The state determination section 47 determines the abnormal state of the driver based on the variation in the breathing cycle and breathing depth.

Figure 9:
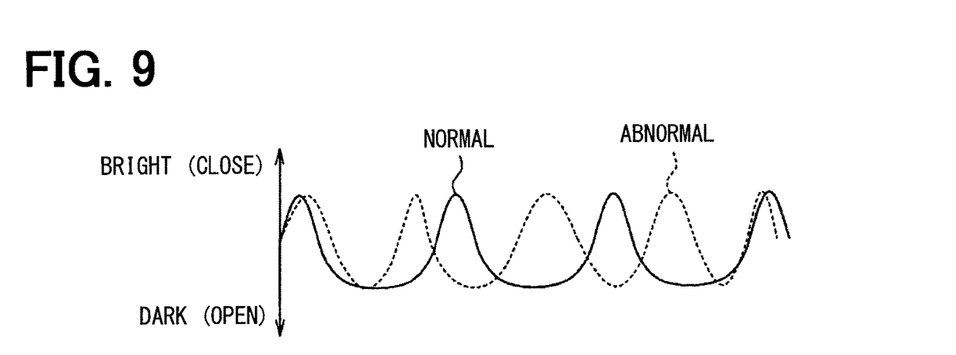
FIG. 9 illustrates blink states in a normal state and an abnormal state.

As in FIG. 9, when the driver is normal, the blink cycle and average eye closure time indicate stable generally-constant values. When the driver is abnormal, the blink cycle and average eye closure time change from the normal state to vary unstably. The state determination section 47 determines the abnormal state of the driver based on the variations in the blink cycle and average eye closure time and on the variation in the eye opening degree such as continuation of the half-eye state. Detection of the half eye is found from an area variation of a dark portion in the eye search area.

Figure 10:
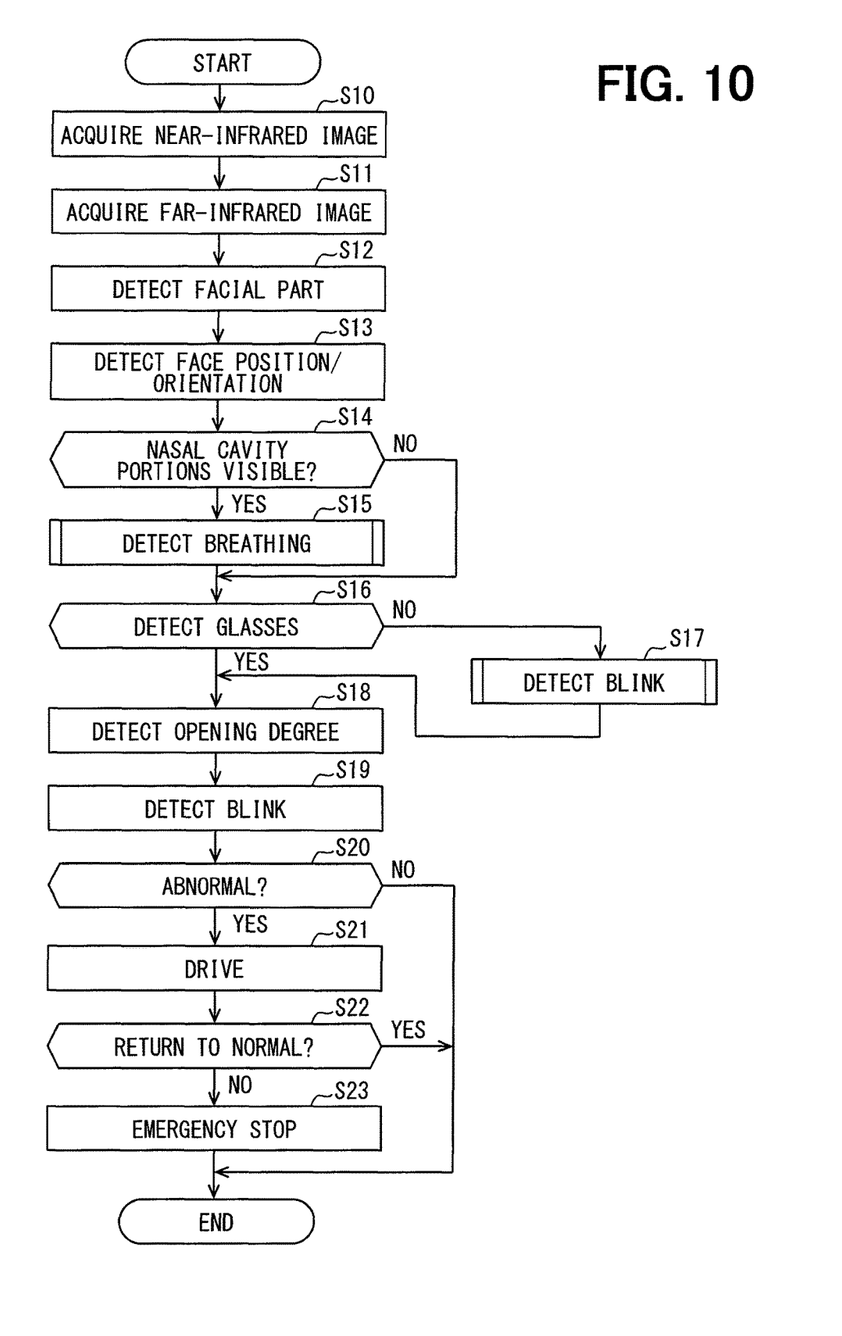
FIG. 10 illustrates a flowchart indicating a procedure of detecting an abnormal state of a driver.

Next, a procedure that determines the abnormal state of the driver is explained with reference to the flowchart of FIG. 10. The ECU 20 repeats the present procedure.

First, the near-infrared image taken by the near-infrared camera 12 (S10) is acquired, and the far-infrared image taken by the far-infrared camera 11 is acquired (S11). The processes of S10 and S11 may be reversed in order as long as executed at the substantially same time. Not in every image taking but sometimes, the far-infrared camera 11 needs to be reset by a shutter due to its characteristic. A frame loss may thus occur. This is processed appropriately. Here, "S" signifies a section or a step.

Then, the facial parts, namely, the eyes, nose, and mouth are detected from the near-infrared image acquired at S10. In detail, the facial parts are recognized in the near-infrared image, and the positional informations on the facial parts are acquired (S12). Then, the position and orientation of the face are detected (S13) based on arrangement of the facial parts detected at S12 (S13). When the position of the detected face is not within the far-infrared image, the processes (S14 to S17) based on the far-infrared image are not performed.

Then, it is determined whether the face detected at S13 is oriented such that the nasal cavity portions are visible (S14). When the face detected at S13 is oriented such that the nasal cavity portions are visible (S14: YES), the breathing state is detected based on the far-infrared image acquired at S11 (S15). The procedure of the breathing state detection is described later in detail. When the face detected at S13 is oriented such that the nasal cavity portions are invisible (S14: NO), the processing proceeds to the glasses detection without performing the breathing state detection.

Then, it is determined whether the glasses are detected from the far-infrared image acquired at S11 (S16). When the glasses are not detected (S16: NO), the blink state detection is performed based on the far-infrared image acquired at S11 (S17). The procedure of the blink state detection is described later in detail. After S17, the eye opening degrees of the eyes of the driver are detected from the near-infrared image acquired at S10 (S18). In contrast, when the glasses are detected (S16: YES), the eye opening degrees of the eyes of the driver are detected from the near-infrared image acquired at S10 without performing the blink state detection based on the far-infrared image acquired at S11 (S18).

When the glasses are detected at S16, the frame of the glasses can be prevented from being falsely detected as the outlines of the eyes by using the informations on the presence and position of the glasses detected at S16 in detecting the eye opening degrees from the near-infrared image acquired at S10. The variation in the eye opening degree during a predetermined period is calculated using a history of eye opening degrees and the eye opening degree detected at S18. The blink cycle is detected from the calculated variation in the eye opening degree (S19).

Then, based on the breathing cycle detected at S15 and/or the blink cycle detected at S17 and/or S19, it is determined whether the driver is abnormal (S20). The detected breathing cycle and blink cycle are learned. When a difference between the detected breathing cycle and a learning value of the breathing cycle is greater than a breathing threshold or when a difference between the detected blink cycle and a learning value of the blink cycle is greater than a blink threshold, it is determined that the driver is abnormal. Alternatively, when a variance value of the detected breathing cycles is greater than a breathing variance threshold or when a variance value of the detected blink cycles is greater than a blink variance threshold, it may be determined that the driver is abnormal. Additionally, an abnormality degree of each of the detected breathing cycle and blink cycle may be calculated to integrate the calculated abnormality degrees. The integrated abnormality degree may be then compared to an abnormality threshold to determine the abnormal state of the driver. When the breathing state is not detected at S15, the abnormal state of the driver is determined only based on the blink state.

It is determined whether the driver is abnormal based on the facial orientation detected at S13 (S20). When the face of the driver is oriented to look aside, it is determined that the driver is abnormal.

When it is determined that the driver is normal at S20 (S20: NO), the present processing ends. When it is determined that the driver is abnormal at S20 (S20: YES), a control signal is transmitted to each apparatus 61 to 63 of the actuator group 60 to drive each apparatus 61 to 63 (S21).

Then, the processes S11 to S20 are repeated to determine whether the driver returns to the normal state (S22). When the driver returns to the normal state (S22: YES), the present processing ends. When the driver remains abnormal (S22: NO), a control signal is transmitted to the vehicle emergency stop apparatus 64 to emergency stop the vehicle (S23). Then, the present processing ends.

Figure 11:
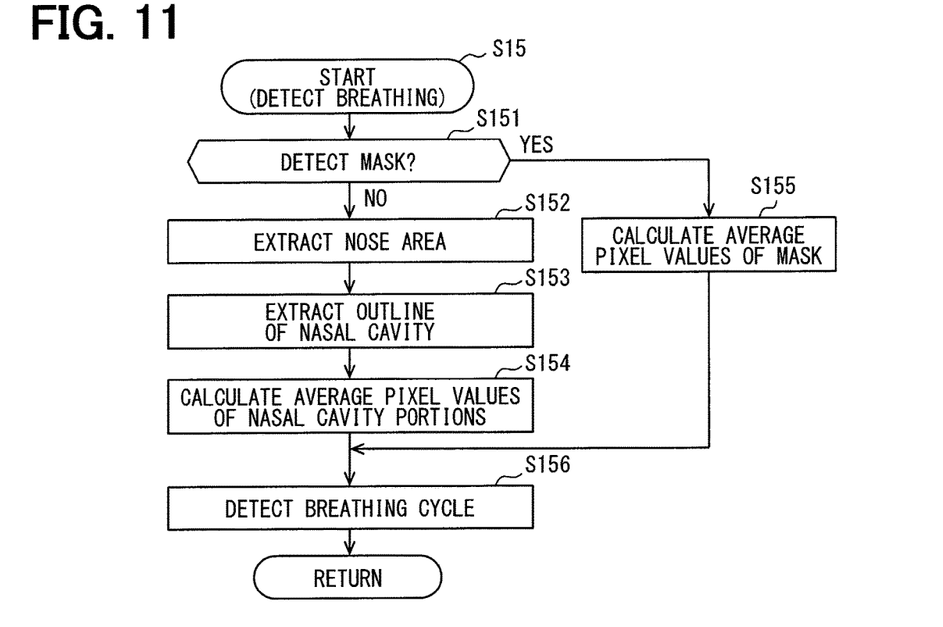
FIG. 11 illustrates a subroutine indicating a procedure of detecting a breathing state.

A procedure of the breathing state detection is explained with reference to a subroutine of FIG. 11. First, it is determined whether the mask is detected from the far-infrared image acquired at S11 (S151).

When no mask is detected (S151: NO), the nose area N to search for the nasal cavity portions is extracted from the far-infrared image acquired at S11 by using the positional information on the nose acquired at S12 (S152). The nose area N extracted at S152 is searched to detect the outlines of the nasal cavity portions (S153). Since one of the two nasal cavity portions may be clogged, the left and right nasal cavity portions are detected respectively. Pixel values in each outline of the right and left nasal cavity portions detected at S153 are averaged to calculate average pixel values of the left and right nasal cavity portions (S154). Then, a history of average pixel values of the left and right nasal cavity portions and the average pixel values calculated at S154 are used to calculate the variations in the right and left average pixel values during a predetermined period and to thereby detect the breathing cycle (S156). The breathing cycle is detectable even when one nasal cavity portion is clogged because the breathing cycles of the left and right nasal cavity portions are detected respectively. Then, the processing proceeds to S16.

When the right and left average pixel values indicate little variation during the predetermined period, it is determined that the driver breaths through the mouth instead of the nose. In this case, the mouth area M is extracted from the far-infrared image acquired at S11, and searched to detect the outline of the mouth. The breathing cycle is detected by calculating a pixel average in the mouth portion and variation in the pixel average in the mouth portion during a predetermined period.

When the mask is detected (S151: YES), an average of the pixel values in the portion covering the nose and mouth in the detected mask (S155). The variation in the pixel average during a predetermined period is calculated to detect the breathing cycle (S156) by using a history of brightness averages of the mask and the average of the pixel values calculated at S155 in the whole mask or in the area where the nose and mouth are estimated to be present in the mask. Then, the processing proceeds to S16.

Figure 12:
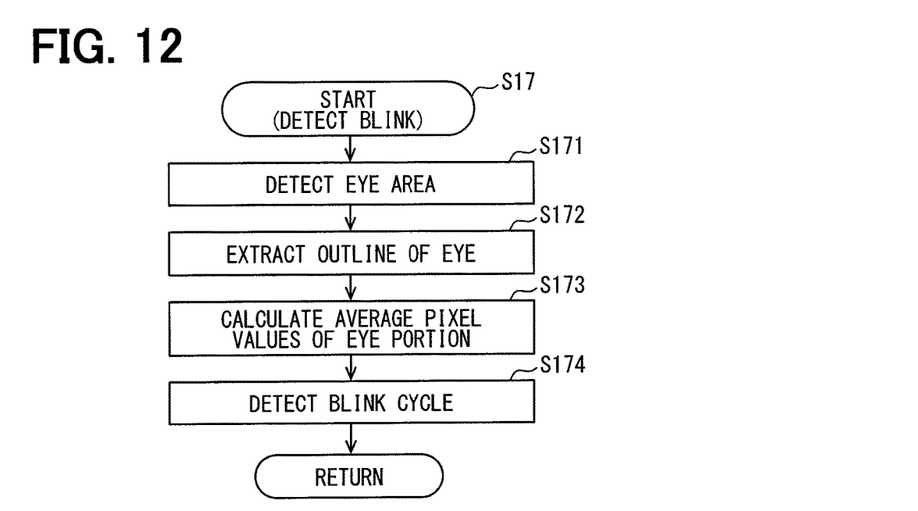
FIG. 12 illustrates a subroutine indicating a procedure of detecting a blink state.

Next, a procedure of the blink state detection is explained with reference to the subroutine of FIG. 12. First, the eye areas El, Er to search for the eye portions are extracted from the far-infrared image acquired at S11 by using the positional information on the eyes acquired at S12 (S171). The eye areas El, Er extracted at S171 are searched to detect the outlines of the left and right eyes (S172). Then, an average of pixel values in the outline of the left eye portion detected at S172 and an average of pixel values in the outline of the right eye portion detected at S172 are calculated (S173). Then, by using a history of the pixel averages of the eye portions and the pixel averages of the eye portions calculated at S173, the variations in the pixel averages of the eye portions in a predetermined period are calculated to detect the blink cycle (S174). Then, the processing proceeds to S18.

The above present embodiment achieves the following effects.

The far-infrared camera 11 takes the far-infrared images indicating temperature distributions on the facial surface of the driver. When the driver becomes abnormal, the temperature distribution of the face of the driver locally varies differently from that when the driver is normal. Therefore, the abnormal state of the driver can be determined based on the far-infrared images sequentially taken during a predetermined period. The far-infrared camera 11 is less susceptible to ambient light. The far-infrared camera 11, which is a non-contact sensor, can take facial images of the driver stably. Therefore, the abnormal state of the driver can be determined accurately from the far-infrared images of the face of the driver during a predetermined period.

The temperatures of the nasal cavity portions or mouth portion vary in response to the breathing cycle. Therefore, the breathing state of the driver is detectable from the temperature variation informations on the nasal cavity portions or mouth portion of the driver. The abnormal state of the driver can be determined from the detected breathing state of the driver.

The temperatures of the eye portions vary in response to the blink cycle. Therefore, the blink state of the driver is detectable from the temperature variation informations on the eye portions of the driver. The abnormal state of the driver can be determined from the detected blink state of the driver.

When the driver becomes abnormal, the breathing cycle changes from the normal breathing cycle or varies. Therefore, the abnormal state of the driver can be determined based on the variation in the breathing cycle.

When the driver becomes abnormal, the blink cycle changes from the normal blink cycle or varies. Therefore, the abnormal state of the driver can be determined based on the variation in the blink cycle.

It is difficult to recognize facial parts from the far-infrared images in usual image processing because the far-infrared images are unclear as images. In contrast, edge points of facial parts are extracted from the near-infrared images for easy recognition of the facial parts. Then, the facial parts are recognized from the near-infrared images taken by the near-infrared camera 12 to acquire the positional informations on the facial parts. The eye areas El, Er, nose area N, and mouth area M in the far-infrared images are extracted using the positional informations on the facial parts acquired from the near-infrared images. Thus, the multi-modal detection technique having the combination of the far-infrared camera 11 and near-infrared camera 12 is used to enable more accurate detection of the breathing state and blink state of the driver than when only the far-infrared camera 11 is used.

It is usually difficult to detect a mask from the near-infrared images. Since the temperature of the mask portion covering the nose and mouth entirely varies with breathing in the far-infrared images, the mask can be detected from the far-infrared images accurately.

Glasses usually appear darker than the other facial parts in the far-infrared images. The glasses are therefore accurately detectable from the far-infrared images.

When the driver wears a mask, the nose area N or mouth area M cannot be extracted, but the mask entirely varies in temperature with breathing. Then, when the mask is detected, the breathing state can be detected from the variation in temperature of the mask as the breathing portion.

When the driver wears glasses, the blink state cannot be detected from the variations in temperatures of the eye portions by using the far-infrared images. In this case, the blink state is detectable from the variation in the eye opening degree by detecting the eye opening degrees from the near-infrared images.

The eye opening degrees of the driver's eyes are detected from the near-infrared images by using the positional informations on the glasses detected from the far-infrared images. The frame of the glasses can be thereby prevented from being falsely detected as the outlines of the eyes.

(Another Embodiment)

The breathing detection section 45 may detect a breathing state such as a breathing depth and a breathing rate instead of the breathing cycle as an index to determine an abnormality of the driver.

The blink detection section 46 may detect a blink state such as an eye closure duration and an average eye opening time as an index to determine an abnormality of the driver.

Only one of the breathing state and blink state may be detected to determine the abnormal state of the driver based on only the detected state.

The state determination circuit 40 of the ECU 20 may include a variation-area detection section 49 that detects, in far-infrared images, a temperature variation area where the amount of variation in temperature during a predetermined period is larger than a threshold. The position acquisition section 41 may extract a recognition area in near-infrared images by using the temperature variation area detected by the variation-area detection section 49 to recognize facial parts in the extracted recognition area. This can reduce the load of the recognition processing.

The driver state determination apparatus 10 may not include the near-infrared camera 12. The abnormal state of the driver may be determined by using only the far-infrared images taken by the far-infrared camera 11. In this case, a pair of left and right portions that repeatedly vary in temperature is detected as eye portions or nasal cavity portions based on a temporal change in the far-infrared images. While the driver is breathing through the mouth, the portion where temperature repeatedly varies below the eyes is detected as the mouth portion.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. A driver state determination apparatus comprising:
   a far-infrared camera that takes facial images of a driver of a vehicle, the facial images being far-infrared images indicating a temperature distribution on a facial surface of the driver;
   a state determination section that determines an abnormal state of the driver based on the far-infrared images sequentially taken by the far-infrared camera during a predetermined period;
   a blink detection section that detects a blink state of the driver from temperature variation information on an eye portion of the driver in the far-infrared images;

a glasses detection section that detects glasses of the driver from the far-infrared images; and a near-infrared camera that takes near-infrared images of the face of the driver, wherein:

the blink detection section detects a blink cycle as the blink state;

when the glasses detection section detects the glasses, the blink detection section detects an eye opening degree of the driver from the near-infrared images and detects the blink cycle from a variation in the detected eye opening degree;

the blink detection section detects an eye opening degree of the driver by using positional information on the glasses detected by the glasses detection section; and the state determination section determines an abnormal state of the driver based on a variation in the blink cycle detected by the blink detection section.

2. The driver state determination apparatus according to claim 1, comprising a breathing detection section that detects a breathing state of the driver from temperature variation information on a breathing portion, the breathing portion being a nasal cavity portion or a mouth portion of the driver in the far-infrared images, wherein the state determination section determines an abnormal state of the driver based on the breathing state detected by the breathing detection section.

3. The driver state determination apparatus according to claim 2, wherein:

the breathing detection section detects a breathing cycle as the breathing state; and the state determination section determines an abnormal state of the driver based on a variation in the breathing cycle.

4. The driver state determination apparatus according to claim 2, comprising:

a position acquisition section that recognizes a nose or a mouth of the driver and acquires positional information on the recognized nose or mouth from the near-infrared images taken by the near-infrared camera; and an area extraction section that extracts a search area to search for the breathing portion in the far-infrared images by using the positional information acquired by the position acquisition section.

5. The driver state determination apparatus according to claim 4, further comprising:

a variation-area detection section that detects a temperature variation area where an amount of variation in temperature during the predetermined period is larger than a threshold in the far-infrared images; and wherein the position acquisition section performs recognition processing by using the temperature variation area detected by the variation-area detection section.

6. The driver state determination apparatus according to claim 2 comprising a mask detection section that detects a mask covering the nose and mouth of the driver from the far-infrared images.

7. The driver state determination apparatus according to claim 6, wherein when the mask is detected by the mask detection section, the detected mask is the breathing portion.

8. The driver state determination apparatus according to claim 2 comprising:

a face orientation detection section that detects a face orientation of the driver from the near-infrared images taken by the near-infrared camera, wherein when a face orientation of the driver detected by the face orientation detection section causes the nasal cavity portion to be invisible by the far-infrared camera, the breathing detection section stops detection of the breathing state.

9. The driver state determination apparatus according to claim 1, comprising:

a position acquisition section that recognizes an eye of the driver and acquires positional information on the recognized eye from the near-infrared images taken by the near-infrared camera; and an area extraction section that extracts a search area to search for the eye portion in the far-infrared images based on the positional information acquired by the position acquisition section.

10. The driver state determination apparatus according to claim 9 comprising:

a variation-area detection section that detects, in the far-infrared images, a temperature variation area where an amount of variation in temperature during the predetermined period is larger than a threshold; and the position acquisition section performs recognition processing by using the temperature variation area detected by the variation-area detection section.

11. A driver state determination apparatus comprising:

a far-infrared camera that takes facial images of a driver of a vehicle, the facial images being far-infrared images indicating a temperature distribution on a facial surface of the driver;

a state determination section that determines an abnormal state of the driver based on the far-infrared images sequentially taken by the far-infrared camera during a predetermined period;

a breathing detection section that detects a breathing state of the driver from temperature variation information on a breathing portion, the breathing portion being a nasal cavity portion or a mouth portion of the driver in the far-infrared images;

a near-infrared camera that takes near-infrared images of a face of the driver;

a position acquisition section that recognizes a nose or a mouth of the driver and acquires positional information on the recognized nose or mouth from the near-infrared images taken by the near-infrared camera;

an area extraction section that extracts a search area to search for the breathing portion in the far-infrared images by using the positional information acquired by the position acquisition section; and a variation-area detection section that detects a temperature variation area where an amount of variation in temperature during the predetermined period is larger than a threshold in the far-infrared images, wherein:

the position acquisition section performs recognition processing by using the temperature variation area detected by the variation-area detection section; and the state determination section determines an abnormal state of the driver based on the breathing state detected by the breathing detection section.

12. The driver state determination apparatus according to claim 11, comprising:

a blink detection section that detects a blink state of the driver from temperature variation information on an eye portion of the driver in the far-infrared images; and a glasses detection section that detects glasses of the driver from the far-infrared images, wherein:

the blink detection section detects a blink cycle as the blink state;

when the glasses detection section detects the glasses, the blink detection section detects an eye opening degree of the driver from the near-infrared images and detects the blink cycle from a variation in the detected eye opening degree; and the state determination section determines an abnormal state of the driver based on a variation in the blink cycle detected by the blink detection section.

13. A driver state determination apparatus comprising:

a far-infrared camera that takes facial images of a driver of a vehicle, the facial images being far-infrared images indicating a temperature distribution on a facial surface of the driver;

a state determination section that determines an abnormal state of the driver based on the far-infrared images sequentially taken by the far-infrared camera during a predetermined period;

a breathing detection section that detects a breathing state of the driver from temperature variation information on a breathing portion, the breathing portion being a nasal cavity portion or a mouth portion of the driver in the far-infrared images, a near-infrared camera that takes near-infrared images of the face of the driver; and a face orientation detection section that detects a face orientation of the driver from the near-infrared images taken by the near-infrared camera, wherein when a face orientation of the driver detected by the face orientation detection section causes the nasal cavity portion to be invisible by the far-infrared camera, wherein:

the breathing detection section stops detection of the breathing state; and the state determination section determines an abnormal state of the driver based on the breathing state detected by the breathing detection section.

14. The driver state determination apparatus according to claim 13, comprising:

a blink detection section that detects a blink state of the driver from temperature variation information on an eye portion of the driver in the far-infrared images; and, a glasses detection section that detects glasses of the driver from the far-infrared images, wherein:

the blink detection section detects a blink cycle as the blink state; and when the glasses detection section detects the glasses, the blink detection section detects an eye opening degree of the driver from the near-infrared images and detects the blink cycle from a variation in the detected eye opening degree; and the state determination section determines an abnormal state of the driver based on a variation in the blink cycle detected by the blink detection section.

\* \* \* \* \*